(12) United States Patent
De Weijer et al.

(10) Patent No.: US 6,710,869 B1
(45) Date of Patent: Mar. 23, 2004

(54) PROCESS FOR DETERMINING THE DYE UPTAKE OF POLYETHYLENE TEREPHTHALATE FIBERS

(75) Inventors: Anton P. De Weijer, Nijmegen (NL); Robert J. Van Wijk, Arnhem (NL); Erik Swieringa, Nijmegen (NL)

(73) Assignee: Acordis Industrial Fibers GmbH, Wuppertal (DE)

( * ) Notice: Subject to any disclaimer, the term of this patent is extended or adjusted under 35 U.S.C. 154(b) by 0 days.

(21) Appl. No.: 09/913,063

(22) PCT Filed: Jan. 26, 2000

(86) PCT No.: PCT/EP00/00591

§ 371 (c)(1), (2), (4) Date: Sep. 27, 2001

(87) PCT Pub. No.: WO00/47980

PCT Pub. Date: Aug. 17, 2000

(30) Foreign Application Priority Data

Feb. 9, 1999 (NL) ................................................ 1011249
Mar. 1, 1999 (NL) ................................................ 1011418

(51) Int. Cl.[7] ............................ G01J 3/44; G01B 11/00
(52) U.S. Cl. ........................ 356/301; 264/408; 264/409
(58) Field of Search .......................... 356/301; 264/408, 264/409

(56) References Cited

U.S. PATENT DOCUMENTS 3,861,129 A  *  1/1975  Doschko ...................... 57/287
4,156,071 A  *  5/1979  Knox ....................... 528/308.2
5,849,232 A  * 12/1998  Ochi et al. .............. 264/172.15

FOREIGN PATENT DOCUMENTS

WO    WO 91/11695    8/1991
WO    WO 99/12019    3/1999

OTHER PUBLICATIONS

Furer, V. L., et al., "Band Intensities in Raman Spectra of Polyethylene Terephthalate and Model Aromatic Complex Esters," Journal of Applied Spectroscopy, vol. 53, No. 4, pp. 1057–1061, Oct. 1990.

Wong, W. F., et al., "Analysis of the deformation of gel–spun polyethylene fibres using Raman spectroscopy," Journal of Materials Science, vol. 29, No. 2, pp. 510–519, Jan. 1994.

Everall, Neil, et al., "Performance Analysis of an Integrated Process Raman Analyzer Using a Multiplexed Transmission Holographic Grating, CCD Detection, and Confocal Fiber–Optic Sampling," Applied Spectroscopy, vol. 49, No. 5, pp. 610–615, May 1995.

Everall, Neil J., "Measurement of Orientation and Crystallinity in Uniaxially Drawn Poly(ethylene terephthalate) Using Polarized Confocal Raman Microscopy," Applied Spectroscopy, vol. 52, No. 12, pp. 1498–1504, Dec. 1998.

* cited by examiner

Primary Examiner—Zandra V. Smith
Assistant Examiner—Gordon J Stock
(74) Attorney, Agent, or Firm—Oliff & Berridge, PLC

(57) ABSTRACT

The invention pertains to a process for determining the dye uptake of polyethylene terephthalate fibers in which the fibers are irradiated with high-intensity monochromatic light. A light-sensitive sensor is used to measure the Raman scattering and compare it with that of an earlier established model on the basis of Raman spectra of polyethylene terephthalate fibers of known composition and structure. A model is used to calculate the density, which constitutes a quantitative measure of the dye uptake. In the calculation use is made of measurement points from a number of regions in the spectral measuring region of 598 to 1900 $cm^{-1}$.

14 Claims, 3 Drawing Sheets

PROCESS FOR DETERMINING THE DYE UPTAKE OF POLYETHYLENE TEREPHTHALATE FIBERS

BACKGROUND OF THE INVENTION

1. Field of the Invention

The invention pertains to a process for determining the dye uptake of polyethylene terephthalate fibres.

2. Description of the Related Art

A well-known, long-used method of determining the dye uptake of polyethylene terephthalate fibres is to employ a comparative test in which various fibre samples have their different uptakes of a standard dye determined. To this end small pieces of yarn of different samples are knitted into a hose. Next, the hose is dyed with a dye critics to the material under critical conditions, i.e., the time during which the knitted hose is contacted with the liquid in which the dye is dissolved is too short to effect full saturation of the hose with dye or complete uptake of the dye from the bath. In addition, such a test employs dyes which have a slow uptake by the fibrous material in question, and the determination is carried out at a comparatively low temperature. The dye uptake is then evaluated visually by indicating whether a yarn sample's dye uptake is superior, inferior or normal as compared with that of the yarn sample next to it. Major drawbacks of this known method are that:

- the results obtained are relative
- the determination is dependent on the person carrying out the test
- the method is complex and time-/labour-intensive
- only comparatively large differences in dye uptake can be made visible Admittedly, it is possible to do away with the subjective elements present in this determination by using photometric equipment (e.g., a HunterLab spectrometer), but it was found that in that case the knitted structure of the hose has a major effect on the determination.

For that reason there is great need for a method of swiftly and simply determining the dye uptake of polyethylene terephthalate fibres in such a manner as will enable an absolute comparison among the fibre samples. The invention now provides a process by which this requirement is satisfied fully or for the most part.

SUMMARY OF THE INVENTION

The invention consists in that in order to determine their dye uptake, the polyethylene terephthalate fibres are irradiated with high-intensity monochromatic light and a light-sensitive sensor is used to measure the Raman scattering and compare it with that of an earlier established model on the basis of Raman spectra of polyethylene terephthalate fibres of known composition and structure, whereupon a model is used to calculate the density, which constitutes a quantitative measure of the dye uptake, use being made in the calculation of measurement points from a number of regions within the spectral measuring range of 598 to 1900 $cm^{-1}$, where out of a total number of measurement points of 100%:

a. 40–100% originates from the spectral region of category X, b. 0–30% originates from the spectral region of category Y, and c. 0–60% originates from the spectral region Q belonging to neither category X nor category Y, the spectral regions of the categories X and Y, respectively, being formed by:

| Category X | Category Y |
|---|---|
| 704–714 $cm^{-1}$ | 796–802 $cm^{-1}$ |
| 876–890 $cm^{-1}$ | 1128–1132 $cm^{-1}$ |
| 984–1056 $cm^{-1}$ | 1292–1382 $cm^{-1}$ |
| 1086–1106 $cm^{-1}$ | 1596–1616 $cm^{-1}$ |
| 1172–1204 $cm^{-1}$ | |
| 1398–1414 $cm^{-1}$ | |
| 1434–1490 $cm^{-1}$ | |
| 1690–1762 $cm^{-1}$ | | and the measurement points from the spectral region of category X originating from at least six out of the eight sub-regions of category X.

The invention also pertains to polyester fibres selected for uniform dye uptake by means of the aforementioned process.

BRIEF DESCRIPTION OF THE DRAWINGS

These and other advantages and features of this invention will be apparent from the following, especially when considered with the accompanying drawings, in which.

DETAILED DESCRIPTION OF THE PREFERRED EMBODIMENTS

Figure 1:
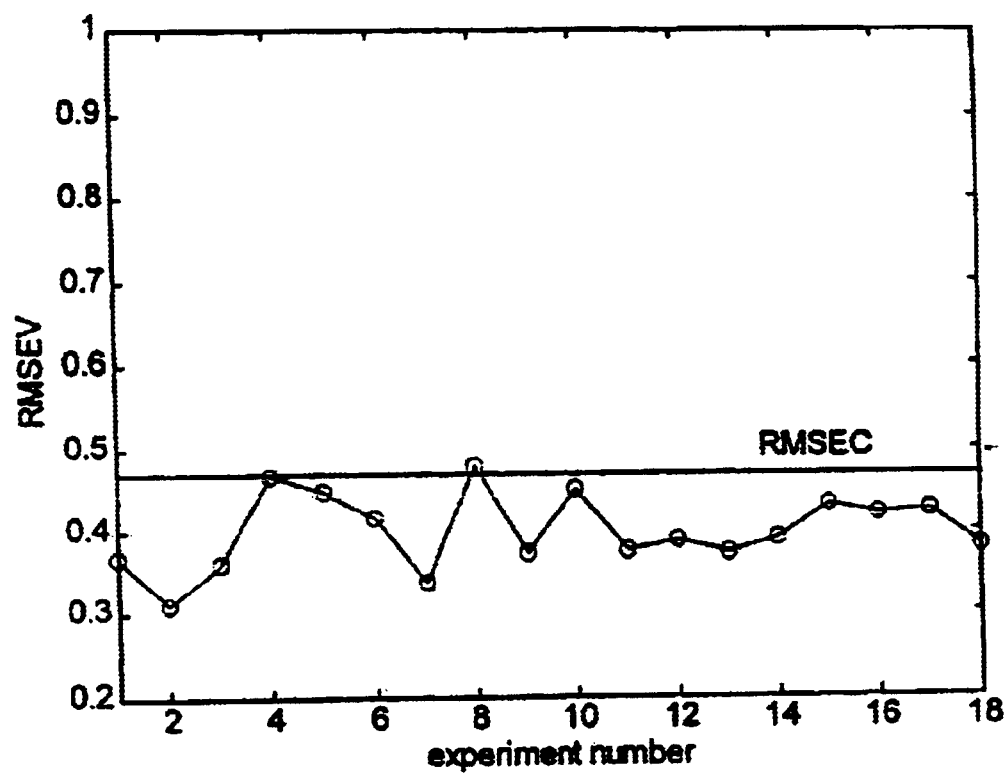
FIG. 1 shows RMSEV of measurements for a model of an example.

According to the present invention, the term polyethylene terephthalate fibres stands for fibres of polyethylene terephthalate obtained by the polycondensation of ethylene glycol with terephthalic acid or an ester-forming equivalent thereof, such as an aliphatic (including cycloaliphatic) or aromatic ester or half-ester, an acid halide or an ammonium salt or amine salt. In addition to ethylene glycol and terephthalic acid, amounts of up to about 10 wt. % of one or more other polyols and/or polycarboxylic acids may be incorporated into the polyethylene terephthalate. Examples of polyols other than ethylene glycol are di- or triethylene glycol and the glycols of the sequence $HO(CH_2)_nOH$, wherein n is an integer from 3 to 10, or polyols having more than two hydroxyl groups, such as pentaerythritol.

It should be noted that measuring Raman spectra to determine particular physical properties on polymers is known as such from an article by N. Everall et al. in *Applied Spectroscopy*, Vol. 49, No.5 (1995), 610–615. In this article it is discussed how the density of polyester films can be predicted on the basis of Raman scattering measurements.

Non-prepublished patent application WO99/12019 discusses a process for determining the dye uptake of fibrous material on the basis of Raman scattering. According to the process described in said document, preferably a Raman spectrum is recorded in the region of 600–2000 $cm^{-1}$ with an optical resolution $\leq 5$ $cm^{-1}$ and a signal-to-noise ratio higher than or equal to 2000, with the baseline of the spectrum being corrected for background radiation. In principle, the entire spectrum across the selected region (598 to 1900 $cm^{-1}$) is used to determine the density and thus the dye uptake. Although the process described in said document gives readily reproducible information about dye uptake, it has since been found that under certain conditions there may be deviations in the measuring result due to the effect of external factors such as changes in yarn tension, changes in ambient temperature, operational variation of the equipment under the influence of the mains voltage, replacement of a laser, etc.

For that reason it has to be deemed extremely surprising that the effect of external interference sources can be eliminated for the most part by selecting from the spectral range of 598 to 1900 $cm^{-1}$, which is more than 1300 $cm^{-1}$ wide, only measurement points from a limited number of precisely described spectral regions.

It was found that when the process according to the invention is employed, the effect of external factors can be reduced still further when in the calculation of the dye uptake it is omitted to use measurement points from the spectral region of the Raman spectrum belonging to category Z and comprising the following wavelength numbers:

| Category Z |
| --- |
| 1056–1086 $cm^{-1}$ |
| 1260–1292 $cm^{-1}$ |
| 1770–1900 $cm^{-1}$ |

As a rule, very favourable results are obtained when the measurement points are selected from the different spectral regions as follows:

a. 45–70% from the spectral region of category X,
b. 10–20% from the spectral region of category Y, and
c. 20–40% from the spectral region Q belonging to neither category X nor category Y.

Optimum results are obtained when the measurement points are selected from the different spectral regions as follows:

a. 50–60% from the spectral region of category X,
b. 10–20% from the spectral region of category Y, and
c. 25–35% from the spectral region Q belonging to neither category X nor category Y.

Within the framework of the invention, the term fibres refers to staple fibres as well as short fibres, filaments, and yarns (an assembly of filaments).

The process according to the invention is not susceptible to the shape of the fibrous material present. Thus the dye uptake of smooth yarns as well as textured yarns can be determined. It is also possible to determine the dye uptake of a collection of short fibres or staple fibres or of fibres having a non-circular cross-section, e.g., a trilobal cross-section. Further, the fibrous material may have been wound, say, on a spool, or it may have undergone additional processing. For instance, it is also possible to determine the dye uptake of fibres in a fabric. In addition, it is possible to measure the dye uptake on non-transparent or dull fibrous material.

Said last material is obtained when small amounts (up to a few per cent) of fillers or pigments such as titanium dioxide have been incorporated into the polyethylene terephthalate.

The only condition which should be placed upon the fibrous material present is that there is a sufficient amount of it to measure an accurate Raman spectrum with the aid of the scattered light in a reproducible manner. If only a small amount of fibrous material is available, this means that measuring a sufficiently accurate Raman spectrum will require a longer measuring time.

The skilled person will be familiar with various ways of making high-intensity monochromatic light available. In the determination according to the invention, it is preferred to use light generated with the aid of a laser, since such light is monochromatic and, depending on the laser's power, of high intensity as well.

When selecting the wavelength of the light used to irradiate the fibrous material, two different phenomena should be taken into account, viz. the reduction of the intensity of the scattered light as the wavelength of the irradiating light increases, and luminescence phenomena exhibited by the fibrous material under the influence of the radiation. Both phenomena are objectionable in that they have a negative effect on the accuracy of the determination. The decreasing intensity of the scattered light (i.e. the Raman signal) is approximately proportional to $1/\lambda^4$, with $\lambda$ being the wavelength of the irradiating light. In which wavelength ranges luminescence phenomena occur is dependent on the chemical composition of the fibrous material. Thus when use is made of a Raman spectrometer with a dispersive medium suitable for industrial application, a too strong attenuation of the scattered light is found in the irradiation of most fibrous materials when the wavelength of the light is more than 900 nm. Although it is possible to irradiate the fibrous material with light having a wavelength of more than 900 nm, detection of the scattered light in that case requires the use of special equipment (FT Raman spectrometer) which at present is suitable for use only under laboratory conditions. A strong luminescence is found when the light's wavelength is less than 600 nm.

In the case of most fibrous materials when using a dispersive Raman spectrometer an optimum in the range of 600 to 900 nm is found for the wavelength of the irradiating light.

In the process according to the invention, a portion of the scattered light is captured with the aid of a lens, and the elastically scattered light is suppressed by a filter. The scattered, filtered light is then passed on via a dispersive medium (for wavelength separation of the scattered light) to a light-sensitive detector so coupled to peripheral equipment that a Raman spectrum can be recorded. Examples of dispersive mediums suitable for use in this process are a prism, a grating, and a holographic grating. As light-sensitive detector may be used, e.g., a CCD-camera or a photomultiplier. It is well-known to the skilled person how these different components should be interconnected to record a Raman spectrum.

For each determination it is of great importance to have the wavelength of the monochromatic light used to irradiate the fibrous material precisely known. Also, it is of great importance to have the wavelength scale of the equipment used to record the Raman spectrum properly calibrated. In this case preference is given to easy-to-use, hence compact equipment containing interference-free dispersive mediums and light-sensitive detectors. One example of compact equipment capable of generating laser light as well as measuring Raman scattering is available from Kaiser Optical Systems, Inc. under the name HoloProbe Process Raman Analyzer 785™.

For greater reproducibility of the results it is preferred to install the Raman equipment in a chamber where the temperature is kept constant within specified limits. Preferably, the Raman equipment will be present in a compartment where the temperature does not vary by more than 4 and preferably 2° C. The laser light and the reflected light can be passed to and from the fibrous material to be measured by means of fibre-optical cables, so that it is not required that the fibrous material to be measured is present in the same space as the Raman equipment.

The detection of the scattered light involves spectral separation of the light and its projection on a matrix of light-sensitive cells (pixels) in a CCD camera. In this way a correlation is achieved between the intensity of the received light and its position in the CCD camera.

To determine the dye uptake of fibres it is of great importance to have the relation between the light's wavelength and the displayed position of the light on the matrix in the CCD camera carefully determined. In the case of continuous measurement, this relation preferably should be determined anew every eight hours. When use is made of the aforementioned HoloProbe Process Raman Analyzer 785™ the spectral lines of a neon light built into the the apparatus are measured for calibration purposes. The correlation between the positions of the spectral lines on the matrix in the CCD camera and their—known—wavelengths is described by adjusting the constants of a polynomial. The appropriate software is included in the control program (HoloGrams) supplied with the HoloProbe Process Raman Analyzer 785™.

To determine the dye uptake it suffices when the obtained Raman spectrum exhibits a signal-to-noise ratio of more than 2000. Here the signal is defined as the highest value in the wavelength region of 600–2000 cm$^{-1}$. Noise in this case is defined as the standard deviation of the differences between the spectra before and after "wavelet smoothing." In "wavelet smoothing" the spectrum is modelled using a linear combination of so-called wavelet basis functions. Coiflet functions are used as wavelet basis functions. To model the spectrum use is made of the waveshrink function with the coiflet C12 of the statistical software package Splus and "soft thresholding."

It proved possible to determine a number of structural parameters of the unknown material with the aid of the found spectrum and the comparison thereof with the spectra of known fibrous materials of the same chemical composition. For textile polyester a clear correlation was found between the density of the fibrous material and the dye uptake.

As a measure of the dye uptake the so-called dyeability index (DI) may be selected, which is defined as follows:

$$DI = \frac{D - D_{min}}{D_{max} - D_{min}} * 10$$

wherein
  D=density of the fibrous material determined from the Raman spectrum,
  $D_{min}$=minimum density of the PET material; generally, the value selected is 1355 kg/m$^3$,
  $D_{max}$=maximum density of the PET material; generally, the value selected is 1405 kg/m$^3$.

In practice, the values of the constants $D_{min}$ and $D_{max}$ are selected such as will give a DI value in the range of 0 to 10.

In order to be able to calculate a quantitative measure of the dye uptake from a found Raman spectrum, first the relation has to be established between the Raman spectra of a number of fibrous materials and their dye uptake. This set of fibrous materials with known dye uptake and known Raman spectrum is also called a calibration set.

This calibration set preferably is selected such that it contains all the variables which can occur in the samples of which the dye uptake needs to be quantified with the aid of the Raman spectrum. In actual practice, such a calibration set will consist of 30–100 samples.

In order to be able to use the calibration set for quantifying the dye uptake of the unknown samples, every sample of the calibration set has its Raman spectrum measured and its density and dye uptake determined in accordance with the dye uptake method described above.

To quantify the dye uptake preferably a Raman spectrum is recorded in the spectral region of 600–2000 cm$^{-1}$ with an optical resolution $\leq$15 cm$^{-1}$ and a signal-to-noise ratio higher than or equal to 2000, with the baseline of the spectrum being corrected for background radiation. Preferably, the optical resolution is in the range of 0.5–10 cm$^{-1}$. Very favourable results were achieved at an optical resolution of 1–7cm$^{-1}$. Preference is given to an optical resolution of 1–7 cm$^{-1}$ at a signal-to-noise ratio >2000.

The number of measurement points which has to be selected to obtain an accurate and robust model is dependent on the optical resolution employed and the number of pixels of the CCD camera on which the spectrum is displayed. The number of pixels on which the spectrum is displayed determines the so-called bin width. Thus at an optical resolution of 5 cm$^{-1}$ and a bin width of 2 cm$^{-1}$ 50–100 measurement points will have to be selected. Preferably, when employing said optical resolution and bin width, 60–80 measurement points are selected. Optimum results are achieved when at said optical resolution and bin width 65–75 measurement points are selected.

So far, optimum results have been achieved when at an optical resolution of the measuring equipment of 1–7 cm$^{-1}$ and a bin width of 2 cm$^{-1}$ use is made in the calculation of information from 64–76 measurement points originating from the following categories:
  a. 36–40 measurement points from the spectral region of category X,
  b. 8–12 measurement points from the spectral region of category Y, and
  c. 20–24 measurement points from the spectral region Q belonging to neither category X nor category Y.

At a bin width of 4 cm$^{-1}$, $(\sqrt{2})^{-1}$ times the aforesaid number of measurement points will have to be selected from each category.

Furthermore, it was found that the robustness of the system can be enhanced significantly when the measurement points from category Q are selected from one or more of the spectral regions of 870–876 and 890–968 cm$^{-1}$.

Various combinations of chemometric treatment steps known to the skilled person can be used to calculate the density and the DI of an unknown yarn sample with the aid of the measured Raman spectrum.

For instance, the measured data can be reduced and scaled by normalising the surface area underneath the measured spectrum in the wavelength region of 1600–1800 cm$^{-1}$. The relationship between the densities of the calibration set and the reduced and scaled spectra can be determined by means of PLS-1 analysis (a PLS analysis with one output variable (also known as "dependent variable"), i.e. the density). PLS in this connection stands for Partial Least Squares. In addition, the entire spectrum can be quantified with the aid of Fourier Transform analysis, in which method for the calibration of the spectrum (by means of PLS-1) use is made of the 60 lowest Fourier coefficients from the analysis. Alternatively, the data in the measured spectra can be scaled and reduced by normalising the surface area of the spectrum in the entire wavelength region, after which the data can be reduced further by means of principal component analysis (PCA), on which the spectrum is calibrated using a multivariate analysis technique such as ANN (Artificial Neural Network). It was found that when PLS is employed, a simple linear model already provides sufficient result in the process according to the invention.

EXAMPLE I (COMPARATIVE EXAMPLE ACCORDING TO WO99/12019)

A set of 84 spools containing polyester yarn was selected from a production process. The set contained 26 spools with yarn showing a low dye uptake in a conventional dye uptake test, 28 spools with yarn with a high dye uptake, and 30 yarns with normal dye uptake. In other respects the spools were selected randomly from the production process over a month's time. The dyeability index of each spool was determined by measuring the density of the yarn in a gradient density column. On each spool containing polyester yarn a Raman spectrum was measured in five different locations, use being made of a HoloProbe Process Raman Analyzer 785™, a product of Kaiser Optical Systems Inc. The transport of the laser light from the HoloProbe to the measurement unit took place with the aid of optical fibres, as did the return transport of the light scattered by the yarn to the HoloProbe. The detection of the scattered light involved spectral separation of the light and its projection on a CCD camera forming part of the HoloProbe. In order to keep the temperature of the optical components of the HoloProbe as constant as possible, the entire measurement unit was cooled. This enabled the temperature in the vicinity of the laser and the CCD camera to be kept constant at a value between 25 and 30° C. To suppress luminescence the samples to be irradiated were exposed to laser light for a few seconds immediately prior to the measurement. The accumulation time of each spectrum was 3 seconds.

For calculation of the model parameters Raman spectra were recorded on all 84 spools while the instrument was at a temperature of 27.5° C., the laser power on the spools at 100 mW, and the laser wavelength, on average over time, at 784.90 nm.

The horizontal axis of each spectrum was converted to Raman shift. The height of the spectrum was determined with a step size of 2 cm$^{-1}$ by interpolation with the aid of a parabola, the constants of the parabola having been adjusted such that it fitted up with four successive points in the spectrum: two upstream of the point of interpolation and two downstream.

From the Raman spectrum in its entirety the region with a Raman shift of 598 to 1900 cm$^{-1}$ was selected. The spectra recorded in five locations on the spool were averaged, to obtain a single Raman spectrum for each spool. The spectra and the dyeability index were mean centered before being used to calculate the model. A PLS (Partial Least Squares) model was calculated, which made it possible to calculate the Dyeability Index. The model complexity was determined with the aid of cross-validation (10 segments of 8 samples and 1 segment of 4 samples).

In order to test the sensitivity of the PLS model to changes in measurement conditions, 20 spools from the set of 84 were selected and their Raman spectra recorded under various conditions. The temperature of the instrument was set to 25, 27.5, and 30° C. and the laser power on the spools to 80, 100, and 120 mW.

Applying the PLS model to the Raman spectra of the 20 selected spools measured in each combination of conditions, the prediction error (RMSEV) of the PLS model was calculated according to the following equation:

$$RMSEV = \left( \sum_{n=1}^{N} \frac{(\hat{y}_n - y_n)^2}{(N-1)} \right)^{\frac{1}{2}}$$

wherein N is the number of measured samples per dataset (20), $\hat{y}_n$ are the DI values as predicted by the employed model, and $y_n$ are the DI values as calculated from the measured densities of the yarns. The results are shown in Table 1.

It is clear from the results (Table 2, column 2) that, in general, the prediction error, RMSEV, increases when the temperature or the laser power changes.

EXAMPLE II

The Raman spectra of Example I were used again in the present example. In the region with a Raman shift of 598 to 1900 cm$^{-1}$ the spectrum was normalised such that the sum of the squares of the channels (652 bins of 2 cm$^{-1}$) was equal to 1. To calculate the Dyeability Index, however, use was made of a model in which only 70 of the 652 measurement points of the spectrum were used as input. Of these measurement points 38 were situated within the spectral region of category X, 10 were situated within the spectral region of category Y, and 22 were situated within the spectral region Q covered by none of X, Y, and Z. The selected measurement points are: 642, 678, 708, 712, 766, 830, 832, 860, 878, 880, 882, 884, 886, 892, 896, 904, 912, 926, 940, 956, 958, 992, 1014, 1020, 1022, 1052, 1088, 1090, 1152, 1160, 1178, 1186, 1190, 1192, 1198, 1220, 1318, 1322, 1326, 1340, 1350, 1376, 1382, 1406, 1410, 1412, 1444, 1462, 1468, 1478, 1482, 1520, 1554, 1566, 1606, 1608, 1614, 1624, 1670, 1692, 1702, 1704, 1714, 1718, 1724, 1730, 1732, 1738, 1742, 1758 cm$^{-1}$.

The spectra and the dyeability index were mean centered before being used to calculate the model. The model parameters were calculated on the basis of the measurements at 27.5° C. and a laser power of 100 mW on all 84 spools and a laser wavelength, on average over time, at 784.90 nm, as described in Example I, introducing only the selected measurement points into the PLS model.

In order to test the sensitivity of the PLS model to the conditions of the measurement; the Raman spectra of 20 spools selected from the set of A4, which were recorded at several combinations of instrument temperature and laser power, as described in Example I, were introduced into the PLS model, using normalised, and only the selected, measurement points. For each set of conditions the prediction error, RMSEV, was calculated as follows:

$$RMSEV = \left( \sum_{n=1}^{N} \frac{(\hat{y}_n - y_n)^2}{(N-1)} \right)^{\frac{1}{2}}$$

wherein N is the number of measured samples per dataset (20), $\hat{y}_n$ are the DI values as predicted by the employed model, and $y_n$ are the DI values as calculated on the basis of the measured yarn densities.

The results are listed in Table 1, together with the results found in the same combinations of conditions in Example I. It is clear from Table 1 (column 3) that this time, in general, the variations in temperature and laser power do not affect the prediction error of the model: the prediction error, RMSEV, is virtually the same in all conditions.

TABLE 1

Prediction error of the models at several combinations of instrument temperature and laser power on the spool

| Varied parameter Laser power/temperature | Example I RMSEV | Example II RMSEV |
| --- | --- | --- |
| 100 mW/25° C. | 0.39 | 0.31 |
| 100 mW/27.5° C. | 0.48 | 0.45 |
| 100 mW/30° C. | 0.58 | 0.48 |
| 80 mW/27.5° C. | 0.82 | 0.47 |
| 120 mW/27.5° C. | 0.65 | 0.42 |

For a further demonstration of the performance of the model according to the invention, Raman spectra were recorded on the 20 selected spools described in Example I, while the conditions of the measurement were varied according to an experimental design. Eighteen experiments were performed according to an experimental set-up in which the temperature of the instrument, the laser power on the spools, and the laser wavelength were varied as specified in Table 2. The laser wavelength was changed by replacing the original laser, which, on average over time, had a wavelength of 784.90 nm, with a laser with an average wavelength of 784.78 nm.

TABLE 2

Experimental design to test the prediction performance of the calculated models in the various examples

| experiment no. | temperature, ° C. | laser wavelength, nm | laser power, mW |
| --- | --- | --- | --- |
| 1 | 25 | 784.90 | 80 |
| 2 | 25 | 784.90 | 100 |
| 3 | 25 | 784.90 | 120 |
| 4 | 27.5 | 784.90 | 80 |
| 5 | 27.5 | 784.90 | 100 |
| 6 | 27.5 | 784.90 | 120 |
| 7 | 30 | 784.90 | 80 |
| 8 | 30 | 784.90 | 100 |
| 9 | 30 | 784.90 | 120 |
| 10 | 25 | 784.78 | 80 |
| 11 | 25 | 784.78 | 100 |
| 12 | 25 | 784.78 | 120 |
| 13 | 27.5 | 784.78 | 80 |
| 14 | 27.5 | 784.78 | 100 |
| 15 | 27.5 | 784.78 | 120 |
| 16 | 30 | 784.78 | 80 |
| 17 | 30 | 784.78 | 100 |
| 18 | 30 | 784.78 | 120 |

In all 18 conditions 5 Raman spectra were recorded in different locations on each of the 20 spools. The spectra were converted as introduced in Example I and II. Subsequently, the predicted DI was calculated by introducing the Raman spectra in the models of Example I and Example II. In the latter case only the prescribed selected measurement points were used for input.

From these results the prediction error of all measurements, $RMSEV_{tot}$, was calculated according to the following equation:

$$RMSEV_{tot} = \left( \frac{1}{M} \sum_{m=1}^{M} \sum_{n=1}^{N} \frac{(\hat{y}_{mn} - y_{mn})^2}{(N-1)} \right)^{\frac{1}{2}}$$

wherein M is the number of situations in the experimental design points (18), N is the number of samples measured per situation (20), $\hat{y}_{mn}$ are the DI values as predicted by the employed model, and $y_{mn}$ are the DI values as calculated on the basis of the measured densities of the samples. The results are shown in Table 3.

Another value demonstrating the performance of the method according to the invention is the calibration error RMSEC. The calibration error RMSEC is a measure of the prediction error of the model for the dataset which was used to calculate the parameters of the model. The calibration error is calculated as follows:

$$RMSEC = \left( \sum_{n=1}^{N} \frac{(\hat{y}_n - y_n)^2}{(N-1-lv)} \right)^{\frac{1}{2}}$$

wherein lv is the number of PLS factors, N the number of samples in the dataset (84), $\hat{y}_n$ are the DI values as predicted by the employed model, and $y_n$ are the DI values as calculated on the basis of the measured yarn densities. The calibration errors of both the model used in Example I and the model of Example II are shown in Table 3.

The errors listed in Table 3 may be compared to the full range of the Dyeability Index of the set of 20 selected PET yarns, which was 2.5 to 8.0. The experimental error (standard deviation) for DI calculated from density measurements was 0.39.

It is clear that when the method according to the invention is used, first of all fewer model parameters are required to generate a sound model. Although the difference between the measured calibration data and the model (RMSEC) is greater when the process according to the invention is employed than for the method according to Example I, it was found that when using the process according to the invention the model is more robust and more capable of predicting the DI, since the $RMSEV_{tot}$ is smaller.

TABLE 3

The robustness of PLS models as expressed in the prediction error $RMSEV_{tot}$, and the calibration error RMSEC, in the method according to the invention and according to the process described in Example I

| Spectral pretreatment | Number of PLS factors (i.e. parameters in the linear model) | RMSEC | $RMSEV_{tot}$ |
| --- | --- | --- | --- |
| Example I | 8 | 0.31 | 0.66 |
| Example II | 3 | 0.47 | 0.40 |

In FIG. 1 the RSMEV of the measurements for the model of Example II is shown for all separate situations in the experimental design. The calibration error RSMEC is also indicated, for reference. It is evident from this figure that for each situation the RMSEV is smaller than about 0.5. This is indicative of a model which is stable for all possible practical situations.

Figure 2:
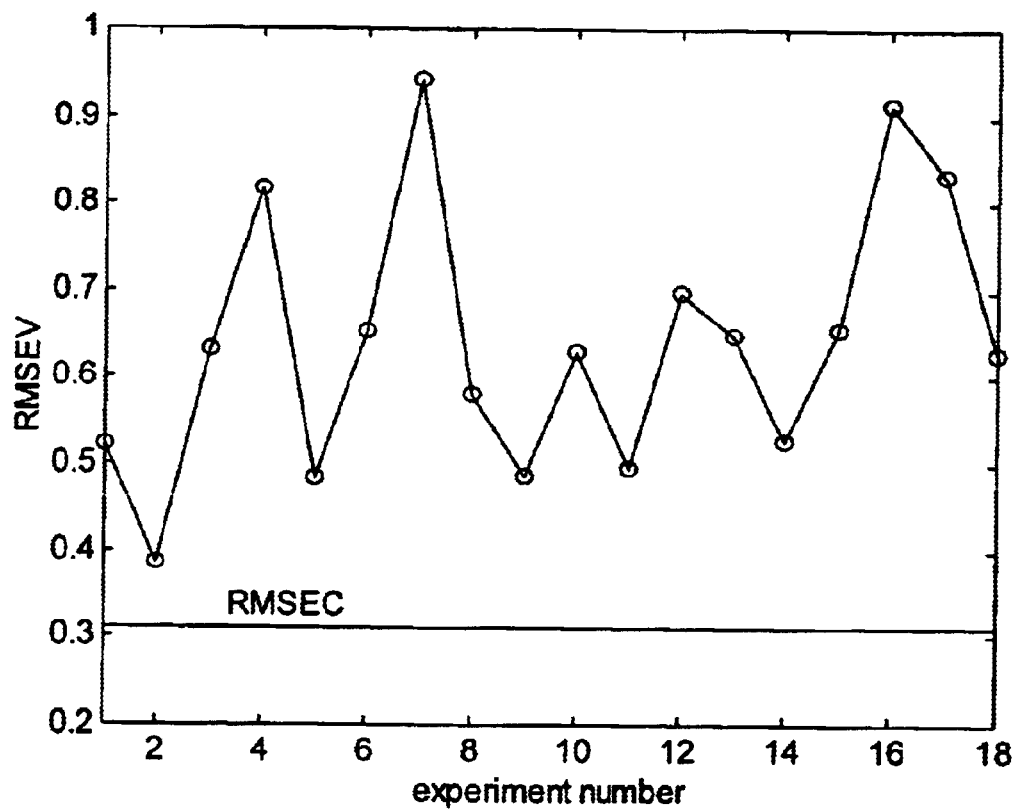
FIG. 2 shows the results of a comparative example.

FIG. 2 shows the results of (Comparative) Example I. It is clear from this figure that a major model error occurs in a number of situations. In practice, this means that in these situations an incorrect production decision may be taken on the basis of the measurements, resulting in one or more spools with a deviating dye uptake going undetected, or good spools being discarded.

EXAMPLE III (COMPARATIVE EXAMPLE)

Figure 3:
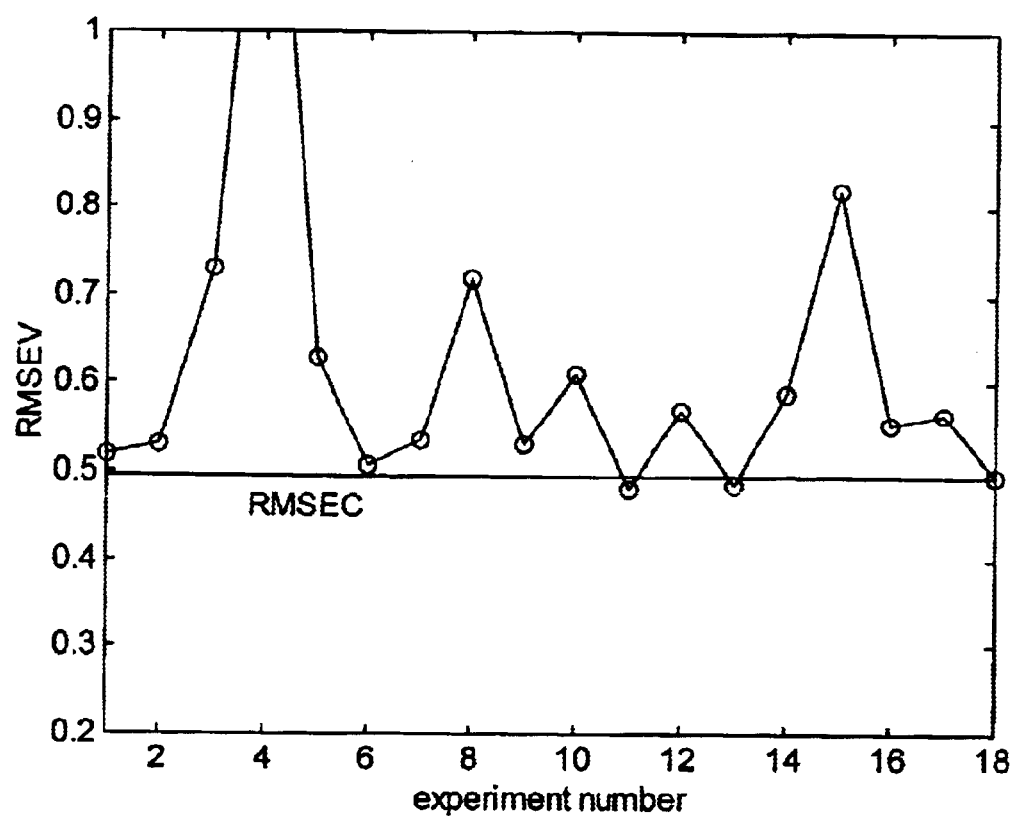
FIG. 3 shows the RMSEV plotted against experiment number for situations of an experimental design.

The Raman spectra recorded on 84 spools as described in Example I were used again in the present example. A model was calculated in a manner analogous to that described in Example II, with the proviso that this time 37% of the measurement points was selected from category Y while 63% was selected from category X. The model was applied to the spectra recorded on a selected set of 20 spools in an experimental design as described in Example II. In FIG. 3 the RMSEV is plotted against the experiment number for the eighteen situations of the experimental design (Table 2). It is clear from this figure that the RMSEC is about the same as the value found in Example II. In other words, the model seems to be well capable of predicting the DI values of the samples used for calibration. On the face of it, the RMSEV does not seem much higher than in Example II. On closer inspection, however, it appears that for a small number of situations a high RMSEV occurs, i.e. substantial differences between the DI value predicted by the model and the measured DI value. For these datasets, in other words, the model proves incapable of predicting a reliable practical dye uptake value.

What is claimed is:

1. A process for determining dye uptake of polyethylene terephthalate fibers, comprising:

irradiating said fibers with high-intensity monochromatic light, measuring Raman scattering using a light-sensitive sensor, and comparing the Raman scattering with an earlier established model of Raman scattering on a basis of Raman spectra of polyethylene terephthalate fibers of known composition and structure, whereupon a density is calculated that constitutes a quantitative measure of the dye uptake, using measurement points from a number of regions in a spectral measuring region of 598 to 1900 $cm^{-1}$, where out of a total number of measurement points of 100%:

(a) 40–100% originates from a spectral region of category X, (b) 0–30% originates from a spectral region of category Y, and (c) 0–60% originates from a spectral region Q belonging to neither category X nor category Y, with the spectral regions of the categories X and Y, respectively, being formed by:

| Category X | Category Y |
| --- | --- |
| 704–714 $cm^{-1}$ | 796–802 $cm^{-1}$ |
| 876–890 $cm^{-1}$ | 1128–1132 $cm^{-1}$ |
| 984–1056 $cm^{-1}$ | 1292–1382 $cm^{-1}$ |
| 1086–1106 $cm^{-1}$ | 1596–1616 $cm^{-1}$ |
| 1172–1204 $cm^{-1}$ | |
| 1398–1414 $cm^{-1}$ | |
| 1434–1490 $cm^{-1}$ | |
| 1690–1762 $cm^{-1}$ | | and the measurement points from the spectral region of category X originate from at least six out of the eight sub-regions of category X.

2. A process according to claim 1, wherein no use is made of measurement points from spectral region of a category Z, which is formed by measurement regions 1056–1086 $cm^{-1}$, 1260–1292 $cm^{-1}$ and 1770–1900 $cm^{-1}$.

3. A process according to claim 1, wherein the measurement points are selected from the different spectral regions as follows:

(a) 45–70% from the spectral region of category X, (b) 10–20% from the spectral region of category Y, and (c) 20–40% from the spectral region Q belonging to neither category X nor category Y.

4. A process according to claim 2, wherein the measurement points are selected from the different spectral regions as follows:

(a) 45–70% from the spectral region of category X, (b) 10–20% from the spectral region of category Y, and (c) 20–40% from the spectral region Q belonging to neither category X nor category Y.

5. A process according to claim 2, wherein the measurement points are selected from the different spectral regions as follows:

(a) 50–60% from the spectral region of category X, (b) 10–20% from the spectral region of category Y, and (c) 25–35% from the spectral region Q belonging to neither category X nor category Y.

6. A process according to claim 2, wherein the calculation at an optical resolution of a measuring equipment of 1–7 $cm^{-1}$ and a bin width of 2 $cm^{-1}$ is made using information from 64–76 measurement points, selected as follows:

(a) 36–40 measurement points from the spectral region of category X, (b) 8–12 measurement points from the spectral region of category Y, and (c) 20–24 measurement points from the spectral region Q belonging to neither category X nor category Y.

7. A process according to claim 1, wherein the measurement points from category Q are selected from the measurement regions 870–876 $cm^{-1}$ and 890–968 $cm^{-1}$.

8. A process according to claim 2, wherein the measurement points from category Q are selected from the measurement regions 870–876 $cm^{-1}$ and 890–968 $cm^{-1}$.

9. A process according to claim 1, wherein the wavelength of the monochromatic light is in the range of 600 to 900 nm.

10. A process according to claim 2, wherein the wavelength of the monochromatic light is in the range of 600 to 900 nm.

11. A process according to claim 1, wherein the resolution of the Raman spectra is 1–7 $cm^{-1}$ at a signal-to-noise ratio $\geq 2000$.

12. A process according to claim 2, wherein the resolution of the Raman spectra is 1–7 $cm^{-1}$ at a signal-to-noise ratio $\geq 2000$.

13. A process for forming and selecting polyethylene terephthalate fibers, comprising:

forming polyethylene terephthalate fibers in a spinning process, determining dye uptake of the formed polyethylene terephthalate fibers by the process according to claim 1, and selecting from among said formed polyethylene terephthalate fibers polyethylene terephthalate fibers having a uniform desired dye uptake.

14. A process for forming and selecting polyethylene terephthalate fibers, comprising:

forming polyethylene terephthalate fibers in a spinning process, determining dye uptake of the formed polyethylene terephthalate fibers by the process according to claim 2, and selecting from among said formed polyethylene terephthalate fibers polyethylene terephthalate fibers having a uniform desired dye uptake.

* * * * *

UNITED STATES PATENT AND TRADEMARK OFFICE
CERTIFICATE OF CORRECTION

PATENT NO. : 6,710,869 B1
DATED : March 23, 2004
INVENTOR(S) : Anton P. De Weijer et al.

It is certified that error appears in the above-identified patent and that said Letters Patent is hereby corrected as shown below:

Column 1,
Lines 16, 25 and 27, change "yam" to -- yarn --;
Line 17, change "critics" to -- critical --;

Column 3,
Line 3, change "yam" to -- yarn --;
Line 44, change "yams" to -- yarns --;
Line 47, change "yams" to -- yarns -- (both occurrences).

Column 6,
Line 47, change "yam" to -- yarn --.

Colunm 7,
Lines 7, 9, 14, 16 and 21, change "yam" to -- yarn --;
Line 10, change "yam" to -- yarn -- and change "yams" to -- yarns --;

Column 8,
Line 10, change "yams" to -- yarns --;
Line 61, change "yam" to -- yarn --.

Column 10,
Line 19, change "yam" to -- yarn --;
Line 24, change "yams" to -- yarns --.

Signed and Sealed this

Thirtieth Day of November, 2004

JON W. DUDAS
*Director of the United States Patent and Trademark Office*